United States Patent
Fischer et al.

(10) Patent No.: US 10,115,485 B2
(45) Date of Patent: Oct. 30, 2018

(54) METHOD OF PLANNING AN EXAMINATION, METHOD OF POSITIONING AN EXAMINATION INSTRUMENT, TOMOSYNTHESIS SYSTEM AND COMPUTER PROGRAM PRODUCT

(71) Applicant: SIEMENS HEALTHCARE GMBH, Erlangen (DE)

(72) Inventors: Daniel Fischer, Heroldsberg (DE); Anna Jerebko, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/617,525

(22) Filed: Jun. 8, 2017

(65) Prior Publication Data

US 2017/0357772 A1    Dec. 14, 2017

(30) Foreign Application Priority Data

Jun. 8, 2016  (DE) .................. 10 2016 210 093

(51) Int. Cl.
| | |
|---|---|
| *G06K 9/00* | (2006.01) |
| *G16H 50/50* | (2018.01) |
| *G06T 7/536* | (2017.01) |
| *G06T 7/73* | (2017.01) |
| *G06F 19/00* | (2018.01) |
| *G06T 11/00* | (2006.01) |

(52) U.S. Cl.
CPC ............ *G16H 50/50* (2018.01); *G06F 19/00* (2013.01); *G06F 19/3481* (2013.01); *G06T 7/536* (2017.01); *G06T 7/75* (2017.01); *G06T 11/008* (2013.01); *G06T 2207/10112* (2013.01); *G06T 2207/30068* (2013.01); *G06T 2207/30096* (2013.01); *G06T 2207/30204* (2013.01); *G06T 2210/41* (2013.01)

(58) Field of Classification Search
None
See application file for complete search history.

(56) References Cited

U.S. PATENT DOCUMENTS

| | | |
|---|---|---|
| 9,401,019 B2 | 7/2016 | Dennerlein et al. |
| 2012/0219109 A1 | 8/2012 | Albanese et al. |

FOREIGN PATENT DOCUMENTS

| | | |
|---|---|---|
| DE | 102015204957 A1 | 10/2015 |
| WO | 2015061582 A2 | 4/2015 |

*Primary Examiner* — Atiba O Fitzpatrick
(74) *Attorney, Agent, or Firm* — Laurence Greenberg; Werner Stemer; Ralph Locher

(57) ABSTRACT

A method for planning an examination of an examination object by a tomosynthesis machine includes: Raw data of the examination object are acquired from defined acquisition angles. An auxiliary data set is reconstructed from the raw data. Depth data are calculated based on the auxiliary data set calculating a number of projections from the perspective of a respectively defined projection center from the auxiliary data set or from the raw data. Each of the projections has a number of image points each linked with associated depth data. The projections are displayed and at least one projection is chosen. A position of an examination region of the examination object is marked therein. A real three-dimensional position of the examination region is calculated using the marked position and its depth data, and an examination path to the examination region is calculated.

12 Claims, 3 Drawing Sheets

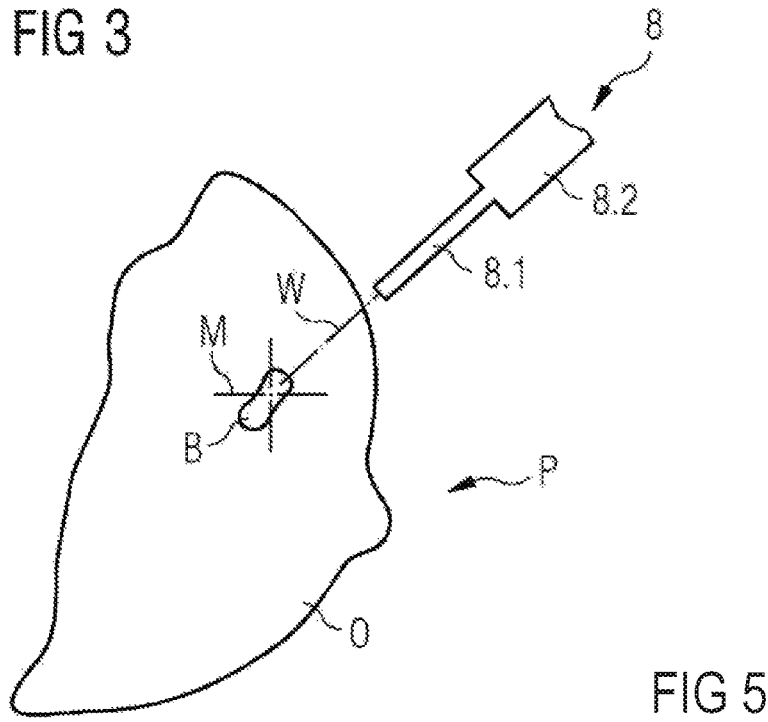
FIG 3
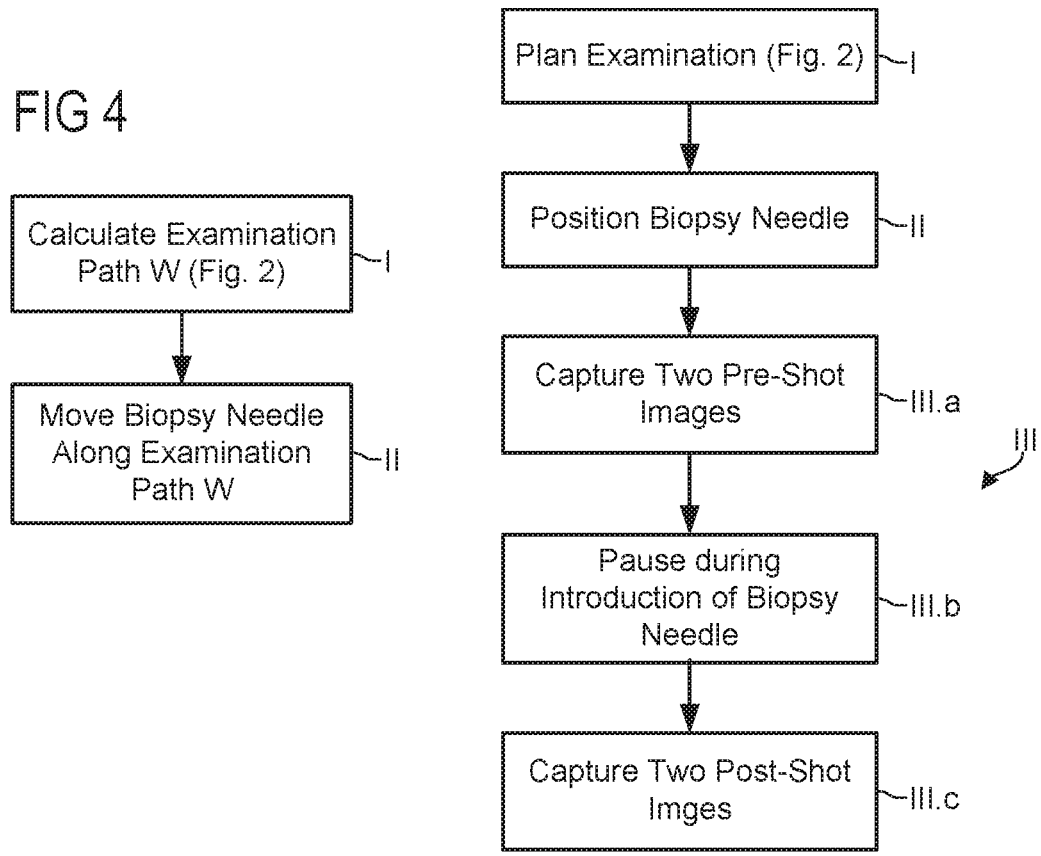
FIG 4
FIG 5

METHOD OF PLANNING AN EXAMINATION, METHOD OF POSITIONING AN EXAMINATION INSTRUMENT, TOMOSYNTHESIS SYSTEM AND COMPUTER PROGRAM PRODUCT

CROSS-REFERENCE TO RELATED APPLICATION

This application claims the priority, under 35 U.S.C. § 119, of German patent application DE 10 2016 210 093.9, filed Jun. 8, 2016; the prior application is herewith incorporated by reference in its entirety.

BACKGROUND OF THE INVENTION

Field of the Invention

The invention relates to a method for planning an examination, to a method for the documentation thereof, to a positioning method and to a tomosynthesis system.

There exist a large number of diagnosis methods for the early detection and recognition of breast cancers. In addition to the conventional medical examination by feel, two-dimensional radiographs, so-called mammograms, are frequently produced as projections of the breast. One problem here is that, owing to the overlaying of different tissue structures, pathological changes in the tissue are often concealed and therefore not recognized. Attempts are made to compensate this problem by recording the breast from two different angles, for example once craniocaudally, i.e. in the direction from the head to the feet, and once at a 45° angle thereto.

The projection images do not provide any information about the malignancy of the change, however. It therefore remains unclear whether a benign or malignant change in tissue is involved. To clarify this, as a rule in the course of a biopsy, a tissue sample has to be taken whose changes in fine-tissue structure are subsequently histologically examined. For the sample taking it is possible to localize the change in tissue using the two mammograms. In order to determine the position in the three-dimensional space it is necessary to mark the change in tissue in both two-dimensional mammograms. The two markings that are to be set result, for example owing to averaging, in a certain level of uncertainty in the localization and this makes the sample taking more difficult.

Furthermore, the technique of what is referred to as tomosynthesis is known. It describes an imaging method in which the breast is recorded from a large number of different angles. For example, projections are acquired at angles of 15 to 50 degrees around the craniocaudal angular position, wherein the total dose substantially matches that of a conventional two-dimensional mammogram. Images for individual slices of the breast tissue are conventionally generated, i.e. reconstructed, from the acquired projection data. The method of filtered back projection is frequently used to reconstruct a volume data set of a region to be examined from the acquired projection data. The resulting volume data set can be viewed slice by slice for diagnosis purposes. Since slices above and below the slice respectively chosen for viewing can be hidden during the diagnosis, pathological changes in tissue are easier to recognize as a rule. However, the slices are shown from just one direction, so, depending on the direction of the change in tissue, it can still be difficult to define and localize it exactly.

SUMMARY OF THE INVENTION

It is accordingly an object of the invention to provide a positioning method and a tomosynthesis system which overcomes the above-mentioned and other disadvantages of the heretofore-known devices and methods of this general type and which enable a simple and accurate three-dimensional localization of a position or location of interest in an examination object by way of a tomosynthesis system in order to plan an examination.

The objects of the invention are achieved by a method for planning an examination, by a positioning method, by a method for the documentation of an examination, by a tomosynthesis system and by a computer program product with computer-executable program code.

With the foregoing and other objects in view there is provided, in accordance with the invention, a method for planning an examination of an examination object by a tomosynthesis machine, the method comprising the following steps:

capturing raw data of the examination object, the raw data having been acquired from a plurality of defined acquisition angles;

reconstructing an auxiliary data set from the raw data;

calculating depth data from the auxiliary data set and calculating a number of projections from a perspective of a respectively defined projection center on a basis of the auxiliary data set or on a basis of the raw data, wherein each of the projections contains a number of image points and each of the image points is linked to the depth data associated therewith, and wherein perspectives of the projections are tilted relative to one another at least on a section of a circular path;

displaying the projections;

enabling at least one projection to be chosen;

marking a position of an examination region of the examination object in the at least one projection thus chosen; and calculating a real three-dimensional position of the examination region using the marked position and the depth data thereof.

The above-mentioned method for planning an examination of an examination object by means of a tomosynthesis machine has the following steps: Firstly, raw data of the examination object are captured which has been acquired from defined acquisition angles. An auxiliary data set is reconstructed from the raw data. Depth data are calculated on the basis of the auxiliary data set. Furthermore, a number of projections are calculated from the perspective of a respectively defined projection center on the basis of the auxiliary data set or on the basis of the raw data. A projection is a virtual view of the captured examination object starting from the virtual projection center as the aspect. The projections each comprise a number of image points and each image point is linked to the depth data associated with it. The projections are then displayed and at least one projection is chosen. A position of an examination region of the examination object is marked in the at least one, preferably exactly one, chosen projection. A real three-dimensional position of the examination region and preferably also an examination path to the examination region is calculated using the marked position and its depth data.

The examination object is, in particular, a body part of a patient, for example a female breast, which is to be examined for pathological changes in tissue. Using the tomosynthesis system firstly, as is conventional with image acquisitions of this kind, raw data are recorded in the form of projections of the examination object. For this X-ray radiation is emitted by an X-ray source, and this penetrates the examination object and is detected by a detector. Different materials that form the examination object generally have different absorption behaviors, so the detector detects information about the structure of the examination object using the projected X-ray radiation. The raw data is recorded from different angles, for example from 9 to 25 angular positions, which are distributed for example with varying angular distances, although preferably equidistantly, over an angular range of ±15° to ±50° about a central angular position, i.e. the acquisition angles are preferably centered around the middle craniocaudal direction (from the head to the feet). An auxiliary image data set, preferably a volume data set, is generated from the raw data acquired in this way. The auxiliary image data set can therefore be obtained as a volume data set using a conventional reconstruction method, for example filtered back projection, which data set is typically used for slice-by-slice presentation of the examination object. The auxiliary data set can, however, also be an abstract data set, i.e. one which cannot be presented directly, from which, for example, only depth data or synthetic projections can be calculated. Using current methods it is, however, also possible to calculate a synthetic projection directly from a number of projections of the raw data.

The volume data set is essentially a three-dimensional image of the examination object. For visualization on a display unit, slice images are usually generated from the set, so only the image information of one slice is displayed while the image information pertaining to the other slices is hidden. By contrast, according to the invention a number of synthetic projections of the examination object is generated. The synthetic projections are not projections in the conventional sense. Instead they preferably highlight the regions of interest of the examination object. The regions of interest have features which regularly represent, for example a change in tissue. The image points of an inventive projection do not generally originate from one plane or slice of the volume data set, but map the regions of interest which can be randomly positioned in the volume data set. The regions of interest can therefore advantageously be viewed in largely all projections. It is therefore no longer necessary to work through slices of interest since the corresponding regions can be seen in any projection.

In theory, a plurality of regions that are potentially of interest can be covered in one projection. In order to be able to distinguish or separate the regions from each other at least in the other projections, one projection center respectively is therefore defined for one projection.

The projection center is the virtual aspect or the perspective of a viewer who is viewing the volume data set along a central viewing direction. This results in a direction of projection relative to the volume data set. This preferably differs between the individual projections. The perspective of the volume data set therefore preferably changes from one projection to another. This prevents the regions of interest from also being covered in different projections.

In addition to standard data, such as, for example, coordinates in the two-dimensional projection image, brightness and/or color or the like, the image points of projections are also linked to depth data. These indicate, for example in the form of a third coordinate, the spacing of the region of interest represented by the image point from the projection center. In any case, the position associated with the image point can be determined therefrom in three dimensions.

The projections obtained in this way can be displayed, for example, as individual images and can therefore be viewed simultaneously or one after the other, in particular by means of "clicking" through the individual images. Additional functions, such as, for example, different color displays and/or a zoom, i.e. an enlargement, can be provided for this. In particular, a region of interest, what is known as an "ROI", can be defined by a viewer in a first projection, and this is accordingly displayed in sections in the subsequent projections (calculated in accordance with this choice). The projections are preferably played back sequentially in the form of a video, however, which can, for example, be stopped and started again as well as sped up and slowed down as the viewer desires. One of the projections is, for example, automatically chosen or chosen by a user by stopping the video.

A position, i.e. an image point or an image region, is automatically marked in the chosen projection, for example using a suitable algorithm. An operator preferably marks the position manually, however, for example by clicking a mouse or selection on a touch screen. The position is located as centrally as possible in a region of interest, in which, for example, a pathological change in tissue is suspected. According to the invention a set marking is already sufficient for the subsequent method steps. However, it is also possible to choose a plurality of projections, to set markings for the same position in these projections. A higher level of accuracy can optionally be achieved hereby.

The position in the volume data set is calculated as described above with the aid of the coordinates of the image point of the marked position and the depth data associated therewith. This represents a position in the real examination object, so the real three-dimensional position can be calculated therefrom, for example by means of a suitable coordinate transformation. The term "real" means that a position is determined in the tangibly existent examination object. An examination path to this position is preferably also calculated on this basis. Other parameters in addition to the position can also be incorporated in the calculation of an optimally advantageous examination path, e.g. for a biopsy needle. For example, tissue properties on a potential examination path, such as the position of blood vessels and/or the possibility of positioning an examination instrument and the like can be taken into account.

With the positioning method mentioned in the introduction, an examination path is calculated using the inventive method for planning an examination and an examination instrument is positioned on the basis of the calculated examination path. The examination instrument is preferably a biopsy device for taking a tissue sample. This comprises a positioning device, a needle holder and a biopsy needle. The positioning device is designed, for example, in the form of a robotic arm, with motoric or hinged elements in such a way that it positions the needle holder and the biopsy needle in accordance with the examination path, in particular on an elongated axis of the examination path. For this the biopsy needle is oriented in such a way that it can advance along the examination path into the tissue in order to remove a tissue sample, for example by means of a vacuum biopsy, in the examination region.

The method mentioned in the introduction for documentation of an examination by means of digital tomosynthesis of an examination object has the following steps: First, the examination is planned using the inventive method for planning an examination. An examination instrument is positioned, in particular using the inventive positioning method. Subsequent actual sample taking by introduction of an examination instrument, for example a biopsy needle, can then take place using a conventional method. At least two projection data sets and/or a tomosynthesis scan, which have/has been acquired before, during and/or after introduction into the examination object and in different operating states (e.g. before and/or after the "launching" of the biopsy needle) of the examination instrument, can then be acquired.

The projections or the tomosynthesis scan acquired before the introduction of the examination instrument or previously determined operating states constitute control radiographs for the examination instrument having been correctly positioned. When the instrument is not exactly positioned the previous steps of marking the region of interest or positioning are repeated in order to be able to optimally carry out the examination. The control radiographs which are acquired after introduction of the examination instrument or after particular operating states are used for control to check that the examination instrument has also actually passed along the planned path to the marked position in the region of interest.

The acquired control radiographs are combined with the volume data set in such a way that the examination instrument is displayed in its respective position in the calculated projections of the original volume data set. On the one hand, it is therefore basically no longer necessary to perform a complete additional tomosynthesis scan for each position of the examination instrument that is to be checked because the inventive method for documentation of an examination enables the data of the control radiographs to be aligned with the original data and be incorporated therein accordingly. This advantageously reduces the resultant radiation exposure. On the other hand, one advantage of a further tomosyntheis scan aligned with the original volume data set is that it can provide much more detailed information about the examination than was previously possible. The type of control radiograph that is to be affected should therefore be weighed up according to the situation.

The tomosynthesis system mentioned in the introduction has a tomosynthesis machine with a source-detector arrangement which is designed for recording raw data of the examination object from defined acquisition angles. Furthermore, the tomosynthesis system comprises a display unit, an input device and an image reconstruction device which is designed in such a way that it carries out the inventive method for planning an examination. For carrying out am inventive positioning method, the tomosynthesis system preferably also has a controller and a corresponding examination instrument having a needle holder and a biopsy needle which can be positioned by means of a positioning device.

The fundamental components of the inventive image reconstruction device can be designed for the most part in the form of software components. Basically, these components can, however, in part, also be implemented in the form of software-assisted hardware, for example FPGAs (field-programmable gate arrays) or the like, especially when particularly fast calculations are involved. The necessary interfaces, for example when only an acquisition of data from other software components is involved, can likewise be designed as software interfaces. They can, however, also be designed as interfaces constructed in terms of hardware which are controlled by appropriate software.

In a particularly useful implementation, the inventive image reconstruction device can be part of a user terminal of a tomosynthesis system.

An implementation largely in terms of software has the advantage that even previously used image reconstruction devices can be easily upgraded by way of a software update in order to work inventively. In this respect the object is also achieved by a corresponding computer program product having a computer program which can be loaded directly into a storage device of an image reconstruction device of a tomosynthesis system, having program segments to carry out all steps of the inventive method when the computer program is run in the image reconstruction device. In addition to the computer program, a computer program product of this kind can optionally comprise additional components, such as, e.g. documentation and/or additional components, also hardware components, such as, e.g. hardware keys (dongles, etc.), for use of the software.

A computer-readable medium, for example, a memory stick, a hard disk or another transportable or permanently installed data carrier, on which the program segments of the computer program that can be read and executed by a processing unit of the image reconstruction device are stored, can be used for transport to the image reconstruction device and/or for storing on or in the image reconstruction device. For this purpose the processing unit can have, e.g., one or more collaborating microprocessor(s) or the like.

Further, particularly advantageous embodiments and developments of the invention result from the dependent claims and the following description, wherein the independent claims of one category can also be developed analogously to the dependent claims of a different category and, in particular, individual features of different exemplary embodiments or variants can also be combined to form new exemplary embodiments or variants.

In one exemplary embodiment of the inventive method for planning an examination, in order to calculate the projection for a large number of rays, which issue from the projection center, one volume image point incorporated by the volume data set is used in each case per ray, which point has an intensity that is at a maximum along the ray. A ray should here be taken to mean a half-line emanating from the projection center and which runs through the image point of the projection associated with it. The ray is therefore not X-ray radiation, but a geometric construction means for calculating the projection. With this type of projection, also called MIP "maximum intensity projection", only those image points of the volume data set are displayed whose equivalence in the examination object has the highest absorption coefficient along the ray. The maximum intensity does not correspond to the intensity of the actually detected X-ray radiation therefore, but to a brightness value which correlates with the absorption of the volume image point that absorbs the most X-ray radiation along the ray. This enables improved presentation of calcifications which are an indication of pathological changes in tissue.

In a further advantageous embodiment of the inventive method for planning an examination, in order to calculate a projection for a large number of rays, which issue from the projection center, one volume image point incorporated by the volume data set is used in each case per ray for which a weighting function is maximum along the ray. Similar to as described above, a point located on the ray is chosen, albeit here on the basis of the weighting function. The weighting function particularly preferably represents features of a structure of the examination object and weights particular structures, namely those of interest, more strongly. Therefore, for example, structures in a defined size regime can be highlighted and the background toned down in contrast.

The weighting function is designed in such a way that it assumes higher values precisely in regions in which the structures of interest are arranged and is maximum in particularly interesting regions. Consequently, the regions or the image points which can indicate, for example, a pathological change in tissue can be selected and highlighted. A detailed image analysis using established means of structural pattern recognition is preferred for generating the weighting function. Different structures, such as e.g. vessels, calcifications, lumps and/or spiculated lumps, i.e. forming points, can therefore be highlighted as required in the weighted mean projection, called HIP "highest interest projection" obtained in this way.

In an advantageous development of the invention the marked position and optionally the examination path is displayed in at least one projection and/or one reconstructed slice image. The determined real position or the determined examination path is therefore displayed as a projection for checking purposes. The position or the examination path can then optionally also be manually optimized or the method repeated once again from the step of marking the position in order to obtain a more advantageous result.

In an inventive method for planning an examination, the examination path is preferably displayed in all projections. This enables an operator to view the marking from different angles and therefore check more efficiently whether it has been sufficiently accurately placed or whether the examination path has been optimally planned.

In an advantageous development of the invention the projection center rotates between the respective projections relatively around the volume data set. Consequently, the perspective, i.e. angle and projection center of the respective projection, is swiveled in relation to the previous projection around the volume data set or around an ROI contained therein. This produces a series of projections whose perspectives are swiveled in relation to each other preferably at least on a section of a, particularly preferably on a complete, circular path around the volume data set. A viewer can therefore advantageously capture the spatial structure of the examination object especially well, in particular with a video presentation of the projections obtained in this way, and this interacts synergistically with the previously described embodiments of the invention.

Other features which are considered as characteristic for the invention are set forth in the appended claims.

Although the invention is illustrated and described herein as embodied in a method for planning an examination, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 shows a view of an exemplary embodiment of an inventively displayed projection;

FIG. 4 shows a block diagram of an exemplary embodiment of an inventive positioning method; and FIG. 5 shows a block diagram of an exemplary embodiment of an inventive method for documentation of an examination.

DETAILED DESCRIPTION OF THE INVENTION

Figure 1:
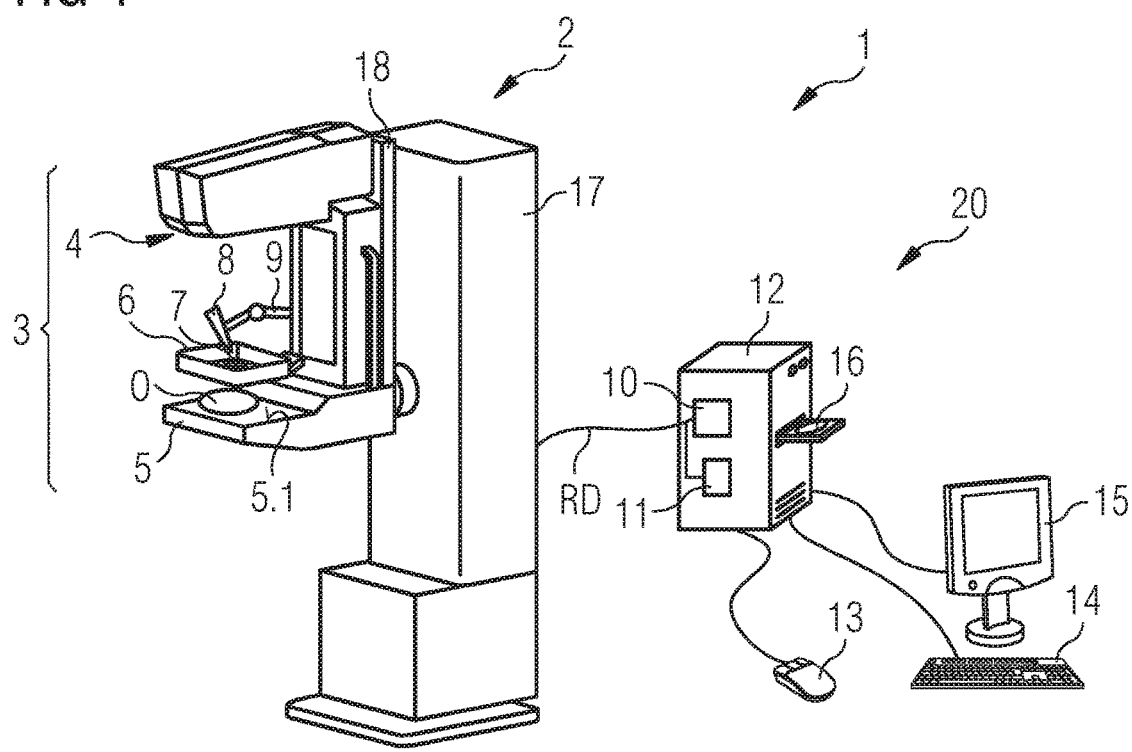
FIG. 1 shows a highly schematic diagram of an exemplary embodiment of a tomosynthesis system according to the invention.

Referring now to the figures of the drawing in detail and first, particularly, to FIG. 1 thereof, there is shown, in a highly schematic illustration, an implementation of a tomosynthesis system 1 according to the invention. Relative directional information, such as above, and, etc. relate to a tomosynthesis system 1 set up as intended for operation. The tomosynthesis system 1 comprises a tomosynthesis machine 2 and a computer system 20. The tomosynthesis machine 2 has a vertical column 17 and source-detector arrangement 3 which in turn comprises an X-ray radiation source 4 and a detector 5 having a detection surface 5.1. During operation, the vertical column 17 stands on the ground. The source-detector arrangement 3 is displaceably connected to the column, so the height of the detector surface 5.1, i.e. the spacing from the ground, can be adjusted to the breast height of a patient.

A breast O of the patient (shown schematically here) rests as an examination object O for an examination on the top side of the detector surface 5.1. A plate 6, which is displaceably connected to the source-detector arrangement 3, is arranged above the breast O and detector surface 5.1. For the examination the breast O is compressed and simultaneously fixed in that the plate 6 is lowered onto it, so pressure is exerted on the breast O between plate 6 and detector surface 5.1. The plate 6 has a circular recess 7 in the middle, through which the breast O can be accessed for the examination.

The X-ray radiation source 4 is arranged so as to oppose the detector 5 and designed such that the detector 5 detects X-ray radiation emitted by it once at least some of the X-ray radiation has penetrated the breast O of the patient. Projections of the breast O are therefore acquired as raw data RD. X-ray radiation source 4 can be swiveled relative to the detector 5 by means of a rotating arm 18 in a range of, for example, ±25° about a basic position in which it is sited perpendicularly above the detection surface 5.1.

In addition, the tomosynthesis machine 2 has a biopsy device 8 as an examination instrument 8 and a robotic arm 9 as a positioning device 9. The robotic arm 9 is connected at a fixed end to the source-detector arrangement 3. It has hinges and motoric elements for positioning the biopsy device 8 which is connected to its free end. The biopsy device 8 comprises a needle holder 8.2 and a biopsy needle 8.1 held therein (see FIG. 3). In order to prepare for a biopsy, i.e. removal of tissue for histological examination, by means of the tomosynthesis system 1, the inventive method for planning an examination is carried out, as described further below.

The computer system 20 comprises a processing unit 12, also referred to as an arithmetic unit or a processor, and a mouse 13, a keyboard 14 and a screen 15 each connected therewith. The screen 15 is used here as a display unit 15; mouse 13 and keyboard 14 are each used as input devices. The processing unit 12 comprises an image reconstruction device 10 and a controller 11 (shown schematically here as blocks) and a drive 16 for reading CDs or DVDs. The image reconstruction device 10 can use the controller 11 shared components of the processing unit 12, such as, e.g. storage devices, processors and the like. The computer system 20 can be arranged in the same space as the tomosynthesis machine 2, but it can also be located in an adjoining control room or in an even more spatially remote location.

Figure 2:
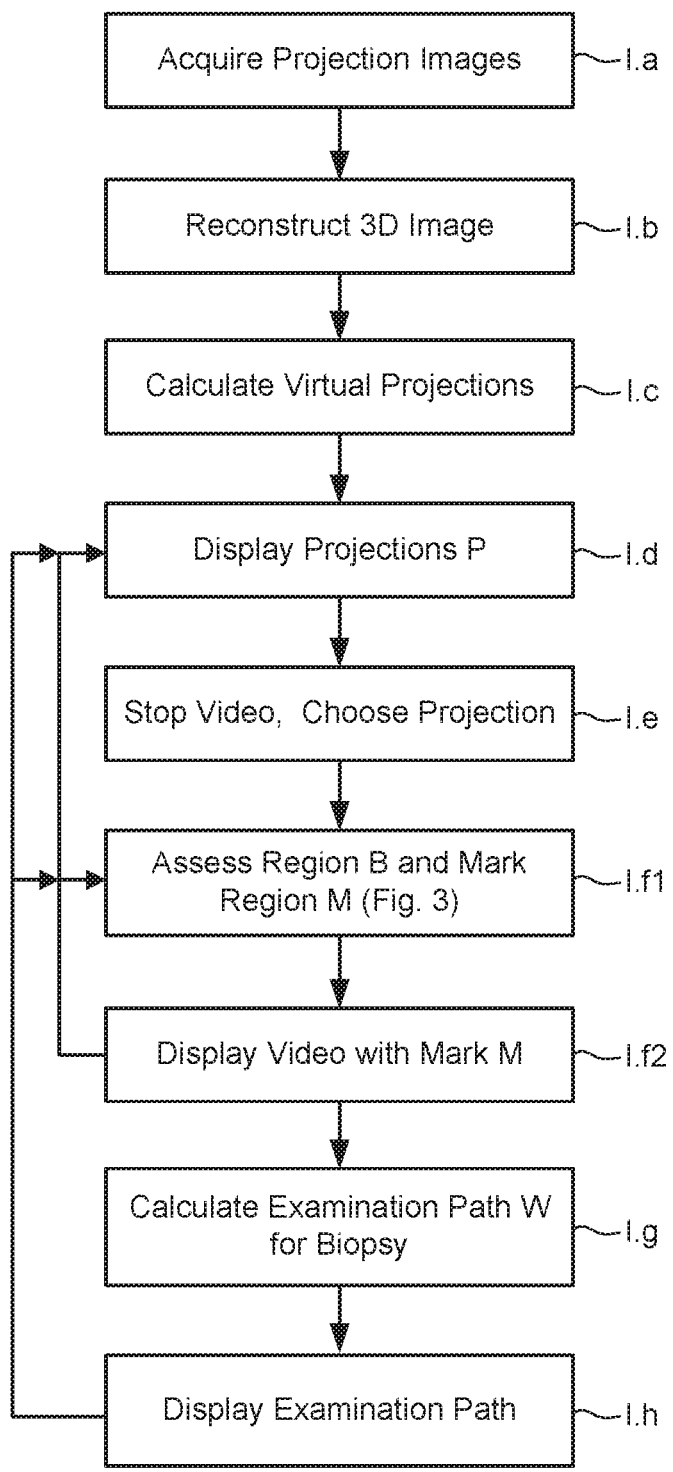
FIG. 2 shows a block diagram of an exemplary embodiment of an inventive method for planning an examination.

FIG. 2 shows by way of example a block diagram of a method for planning an examination I by means of a tomosynthesis machine 2. In a first preparatory step I.a projection images of the breast O are acquired as raw data RD. For this the breast O is firstly compressed and fixed between the plate 6 and the detector surface 5.1. The breast O extends over a larger area as a result of the compression, and this leads to better distinguish ability of individual structures. Fixing serves to prevent movement artifacts. Twenty-five projection images are then acquired from equidistant angles in the range of ±25° around the craniocaudal position, i.e., around the position in which the X-ray source 4 is situated perpendicularly above the detector surface 5.1. More or, to reduce the radiation dose, also fewer projection images can be created as needed, which can optionally also be distributed over a larger or smaller angular range. This raw data RD is transmitted to the processing unit 12.

The actual planning method begins in the second step I.b. A volume data set, i.e. essentially a three-dimensional image of the breast O of the patient, is reconstructed in the image reconstruction unit 10 of the processing unit 12 from the raw data RD by means of the established method of filtered back projection.

In the following third step I.c virtual projections P are calculated from the volume data set. For this the volume data set is viewed virtually from perspectives, i.e. aspects and angles which are regularly arranged on a circular path around the volume data set, i.e., rotated, for example, around the center of the volume data set. Visually this can be described by a circular camera movement having discrete positions around the volume data set.

Especially relevant regions of the volume data set are more strongly weighted in order to assess the malignancy. Depending on the type of change in tissue to be assessed, an MIP (maximum intensity projection) or an HIP (highest interest projection) is applied to the volume data set. (Micro) calcifications, which are distinguished by spatially strongly concentrated high HU values, are preferred with MIP. With HIP, regions are determined and prioritized which, according to their structure, are similar to the change in tissue to be assessed, i.e. lumps, spiculated lumps, etc., by means of a more extensive image analysis using established methods. The points of the volume data set are then displayed in the projection P as image points with their optionally weighted brightness, which along a sight line issuing from the aspect have the highest weighting or the highest priority. The distance of the image points from the aspect is stored, together with the projection P, in the form of a depth map, i.e. as the value associated with the respective image point. Furthermore, the original positions of the image points in the three-dimensional volume of the examination object can be back-calculated from the projection.

The projections P obtained in this way are displayed in the fourth method step I.d on the screen 15 of the tomosynthesis system 1. The display is made in the form of a video rendered from the projections, which displays the breast O in rotation in the projections. In order to choose a projection P in the fifth method step I.e, the video is stopped by way of an input by an operator when the desired projection P is displayed.

The chosen projection P is schematically shown in FIG. 3. The outline or the rough structure can be seen as the projection of the breast O from less strongly stark weighted regions. A region B of interest is located inside the breast O, which contains a change in tissue to be examined and is therefore shown highlighted.

In the following sixth method step I.f1 firstly the region B is assessed by an operator. After a corresponding assessment, the operator marks a position M in the region B in the projection P with the aid of the mouse 13, keyboard 14 or a touch screen, at which position a tissue sample is to be taken. The position M is displayed on the screen 15 so as to be identified by crosshairs or similar marking.

In an optional method step I.f2 the rendered video is displayed again, with the marked position M also being displayed in the projections P this time. The operator can view the marked position M from other angles as well hereby and therefore check its correctness. Step I.f1 is optionally repeated and the marking positioned more accurately or the method returns to step I.d in order to choose a different (more advantageous) projection for the marking.

An examination path W is calculated for the biopsy in the seventh step I.g. This runs in a straight line to the marked position M, with the surrounding tissue being considered in order to keep the necessary damage as minimal as possible.

The examination path W is displayed in the eighth method step I.h on the screen 15 in the two-dimensional projection and incorporated in the (newly) rendered video. Furthermore, a model, i.e. a projection, of the biopsy device 8 is also displayed in the projections P. The biopsy device 8 is incorporated in a position or orientation in the video into which it is brought for the biopsy using a positioning method II shown by FIG. 4. On the basis of this display the operator can assess the progress of the examination path W and optionally return to steps I.d or I.f1 to determine a more advantageous marked position M. The operator can optionally also manually change the examination path W and adapt it to particular circumstances.

FIG. 4 shows, by way of example, a block diagram of an inventive positioning method II. For calculating an examination path W, firstly the method for planning an examination I illustrated with the aid of FIG. 2 is carried out. The biopsy device 8 is subsequently positioned in the positioning method II by means of the robotic arm 9 and the controller 11 on the basis of the examination path W determined in this way. The robotic arm 9 moves the biopsy device 8 by means of hinges and motors relative to the breast O into an angular orientation and position in the three-dimensional space. Thus positioned, the biopsy needle 8.1 held by the needle holder 8.2 advances during the course of a subsequent biopsy exactly to the marked position M in the region B of interest of the breast O.

FIG. 5 shows, by way of example, a block diagram of an inventive method for documentation of an examination III. Firstly, the above-described steps of the method for planning an examination I and the positioning method II are carried out. The biopsy device 8 is then located in the starting position for the subsequent biopsy. In this position, two pre-shot projection images are captured in step III.a, which have been acquired from different angles of the breast O and the biopsy device 8. The method is paused in step III.b to introduce the biopsy needle 8.1 into the breast O in the course of a biopsy (not incorporated by the documentation method). Once the biopsy needle 8.1 has been introduced, in step III.c two post-shot projection images are captured again which have been acquired from different angles of the breast O and the biopsy device 8.

The projection images acquired in steps III.a and III.b are then compared with the original volume data set or registered therewith. Consequently, one video can be generated before the biopsy and one video following introduction of the biopsy needle 8.1 respectively, and these document the respective examination steps more or less three-dimensionally. The radiation exposure for the patient is advantageously kept low despite the extensive documentation, since after the original tomosynthesis scan no further complete scan is acquired and instead only individual projections of the breast are recorded.

Finally, reference is again made to the fact that the devices and methods described above in detail are only exemplary embodiments which can be modified in a wide variety of ways by a person skilled in the art without departing from the scope of the invention. Furthermore, use of the indefinite article "a" or "an" does not preclude the relevant features from also being present several times. Similarly, the terms "device", "unit" and "system" do not preclude the relevant components from comprising a plurality of interacting subcomponents which can optionally also be spatially distributed.

The following is a summary list of reference numerals and the corresponding structure used in the above description of the invention:
- 1 tomosynthesis system
- 2 tomosynthesis machine
- 3 source-detector arrangement
- 4 X-ray radiation source
- 5 detector
- 5.1 detection surface
- 6 plate
- 7 circular recess
- 8 examination instrument, biopsy device
- 8.1 biopsy needle
- 8.2 needle holder
- 9 positioning device, robotic arm
- 10 image reconstruction device
- 11 controller
- 12 processor, arithmetic unit
- 13 mouse
- 14 keyboard
- 15 display unit, screen
- 16 drive
- 17 vertical column
- 18 rotating arm
- 20 computer system
- B region
- M marked position
- O examination object, breast
- P projection
- RD raw data
- W examination path
- I method for planning an examination I.a, . . . , I.h—method steps
- II positioning method
- III method for documentation of an examination IIIa, IIIb, III.b—method steps

The invention claimed is:

1. A method for planning an examination of an examination object by a tomosynthesis machine, the method comprising the following steps:
   a) capturing raw data of the examination object, the raw data having been acquired from a plurality of defined acquisition angles;
   b) reconstructing an auxiliary data set from the raw data;
   c) calculating depth data from the auxiliary data set and calculating a number of projections from a perspective of a respectively defined projection center on a basis of the auxiliary data set or on a basis of the raw data, wherein each of the projections contains a number of image points and each of the image points is linked to the depth data associated therewith, and wherein perspectives of the projections are tilted relative to one another at least on a section of a circular path;
   d) displaying the projections;
   e) enabling at least one projection to be chosen;
   f) marking a position of an examination region of the examination object in the at least one projection thus chosen; and
   g) calculating a real three-dimensional position of the examination region using the marked position and the depth data thereof.

2. The method according to claim 1, which comprises, in order to calculate the projections for a large number of rays that issue from the projection center, using one volume image point incorporated by the volume data set in each case which has an intensity that is at a maximum along the ray.

3. The method according to claim 1, which comprises, in order to calculate a projection for a large number of rays that issue from the projection center, using one volume image point incorporated by the volume data set in each case for which a weighting function is at a maximum along the ray.

4. The method according to claim 3, wherein the weighting function represents features of a structure of the examination object and weights particular structures more strongly.

5. The method according to claim 1, which comprises displaying the marked position in at least one projection and/or in a reconstructed slice image.

6. The method according to claim 1, which comprises displaying the marked position in all projections.

7. The method according to claim 1, which comprises calculating in an examination path to the examination region.

8. A positioning method comprising the following steps:
   calculating a real three-dimensional position of an examination region and an examination path to the examination region by using the method according to claim 1; and
   positioning an examination instrument on a basis of the examination path thus calculated.

9. A method of documenting an examination by a digital tomosynthesis of an examination object, the method comprising the following steps:
   planning the examination by carrying out the method according to claim 1;
   positioning an examination instrument; and
   acquiring at least two projection data sets and/or a tomosynthesis scan, which has been acquired before, during and/or after introduction into the examination object and in different operating states of the examination instrument.

10. A tomosynthesis system, comprising:
    a tomosynthesis machine having a source-detector arrangement configured to record raw data of an examination object from defined acquisition angles; and
    an image reconstruction device connected to said tomosynthesis machine, said image reconstruction device having a display unit and input device, and said image reconstruction device being configured to:
    reconstruct an auxiliary data set from the raw data;
    calculate depth data on a basis of the auxiliary data set and a number of projections from a perspective of a respectively defined projection center on a basis of the auxiliary data set or on a basis of the raw data, wherein each of the projections contains a number of image points and each image point is linked to the depth data associated therewith and wherein perspectives of the projections are swiveled relative to one another on at least a segment of a circular path;

display the projections by way of said display unit, wherein enabling at least one projection to be chosen via said input device;

enabling a position of an examination region of the examination object to be marked by way of the input device in the at least one projection so chosen; and calculating with the image reconstruction device a real three-dimensional position of the examination region using the marked position and the depth data associated therewith.

11. A computer program product, comprising: a non-transitory computer-readable medium storing a computer program to be loaded directly into a storage device of an image reconstruction device of a tomosynthesis system, having program segments configured to carry out the method steps of the method according to claim 1 when the computer program is executed in an image reconstruction device of a tomosynthesis system.

12. A computer-readable medium having program segments stored thereon in non-transitory form that can be read and executed by a processing unit in order to carry out all of the steps of the method according to claim 1 when the program segments are executed by the processing unit.

* * * * *